United States Patent
Shull

(10) Patent No.: US 10,934,590 B2
(45) Date of Patent: Mar. 2, 2021

(54) BIOMARKERS FOR BREAST CANCER AND METHODS OF USE THEREOF

(71) Applicant: WISCONSIN ALUMNI RESEARCH FOUNDATION, Madison, WI (US)

(72) Inventor: James Donald Shull, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 586 days.

(21) Appl. No.: 15/598,856

(22) Filed: May 18, 2017

(65) Prior Publication Data
US 2017/0342502 A1  Nov. 30, 2017

Related U.S. Application Data

(60) Provisional application No. 62/340,693, filed on May 24, 2016.

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 7,526,387 B2 | 4/2009 | Baker et al. | |
| 7,811,774 B2 | 10/2010 | Ring et al. | |
| 7,863,001 B2 | 1/2011 | Dai et al. | |
| 8,632,980 B2 | 1/2014 | Baker et al. | |
| 9,181,588 B2 | 11/2015 | Perou et al. | |
| 2009/0299640 A1* | 12/2009 | Ellis | C12Q 1/6886 702/19 |
| 2011/0145176 A1 | 6/2011 | Perou et al. | |
| 2013/0165343 A1* | 6/2013 | Robinson | C12Q 1/6837 506/9 |

OTHER PUBLICATIONS

Enard et al. (Science 2002 vol. 296 p. 340) (Year: 2002).*
Colletti II, et al.; "Validation of Six Genetic Determinants of Susceptibility to Estrogen-Induced Mammary Cancer in the Rat and Assessment of Their Relevance to Breast Cancer Risk in Humans"; Genes/Genomes/Genetics; 4; pp. 1385-1394; (2014).
Michaud et al.; "Obesity and the Adipocyte; Role of the Agouti Gene in Obesity"; Journal of Endocrinology; 155; pp. 207-209; (1997).
Miltenberger et al.; "The Role of the Agouti Gene in the Yellow Obese Syndrome"; The Journal of Nutrition; 127(9); pp. 1902S-1907S; (1997).
Mynatt et al.; "Agouti Regulates Adipocyte Transcription Factors"; Am J Physiol Cell Physiol; 280; pp. C954-C961; (2001).
Paik et al.; A Multigene Assay to Predict Recurrence of Tamoxifen-treated, Node-negative Breast Cancer; N Engl J Med; 351; pp. 2817-2826; (2004).
Patel et al.; "Melanocortin Receptors as Novel Effectors of Macrophage Responses in Inflammation"; Frontiers in Immunology; 2(41); pp. 1-6; (2011).
Purrington et al.; "Genome-wide Association Study Identifies 25 Known Breast Cancer Susceptibility Loci as Risk Factors for Triple-negative Breast Cancer"; Carcinogenesis; 35(5); pp. 1012-1019; (2014).
Schaffer et al.; "Genetic Bases of Estrogen-Induced Tumorigenesis in the Rat: Mapping of Loci Controlling Susceptibility to Mammary Cancer in a Brown Norway x ACI Intercross"; Cancer Res; 66; pp. 7793-7800; (2006).
Siddiq et al.; "A Meta-analysis of Genome-wide Association Studies of Breast Cancer Identifies Two Novel Susceptibility Loci at 6q14 and 20q11"; Human Molecular Genetics; 21(24); pp. 5373-5384; (2012).
Solin et al.; "A Multigene Expression Assay to Predict Local Recurrence Risk for Ductal Carcinoma In Situ of the Breast"; J Natl Cancer Inst; 105; pp. 701-710; (2013).
Sparano et al.; "Development of the 21-Gene Assay and Its Application in Clinical Practice and Clinical Trials"; Journal of Clinical Oncology; 26(5); pp. 721-728;2008).
Star et al.; "Evidence of Autocrine Modulation of Macrophage Nitric Oxide Synthase by α-melanocyte-stimulating hormone"; Proc. Natl. Acad. Sci. USA; 92; pp. 8016-8020; (1995).
Voisey et al.; "Agouti: from Mouse to Man, From Skin to Fat"; Pigment Cell Res; 15; pp. 10-18; (2002).
Wolff et al.; "Accelerated Appearance of Chemically Induced Mammary Carcinomas in Obese Yellow (Avy/A) (BALB/c X VY) F1 Hybrid Mice"; J. Toxicol Environ Health; 10(1); pp. 131-142; (1982); Abstract only.
Wolff et al.; Manifestation of Hyperplastic Alveolar Nodules and Mammary Tumors in "Viable Yellow" and Non-yellow Mice; J. Natl Cancer Inst.; 63(3); pp. 781-785; (1979); Abstract Only.
Xue et al.; "The Agouti Gene Product Stimulates Pancreatic [beta]-cell Ca2+ Signaling and Insulin Release"; Physiol Genomics; 1(1); 11-19; (1999) Abstract only.
BZ et al.; "The Agouti Gene Product Stimulates Pancreatic [beta]-cell Ca2+ Signaling and Insulin Release"; Physiol Genomics; 1(1); 11-19; (1999) Abstract only.

* cited by examiner

*Primary Examiner* — Katherine D Salmon
(74) *Attorney, Agent, or Firm* — Cantor Colburn LLP

(57) ABSTRACT

Described herein is the use of Agouti Signaling Protein (ASIP), in addition to certain other melanocortin signaling network (MSN) genes, as prognostic and predictive biomarkers for the progression of breast cancer. In particular, the novel biomarkers can be used to determine if a female breast cancer patient is at risk of progressing to metastatic disease and thus also be used to direct treatment of the patient.

9 Claims, 11 Drawing Sheets
Specification includes a Sequence Listing.

BIOMARKERS FOR BREAST CANCER AND METHODS OF USE THEREOF

CROSS-REFERENCE TO RELATED APPLICATIONS

This application claims priority to U.S. Provisional Application 62/340,693 filed on May 24, 2016, which is incorporated herein by reference in its entirety.

FIELD OF THE DISCLOSURE

The present disclosure is related to biomarkers for breast cancer and methods of using the biomarkers to identify and treat patients with DCIS or early stage breast cancer at risk of recurrence and/or progression to metastatic disease.

BACKGROUND

Breast cancer continues to be the most frequently diagnosed cancer (excluding non-melanoma skin cancers) and the second leading cause of cancer related death in American women. Advances in screening and detection have led to increases in the diagnosis of breast ductal carcinoma in situ (DCIS) and early stage invasive breast cancers. A major challenge confronting breast cancer patients and care providers is how to plot the optimal course of treatment for these early stage breast lesions to maximize the likelihood of patient survival while minimizing the adverse effects associated with treating those women whose cancers are likely to be and remain indolent and/or localized. The identification of drivers of progression and function-based biomarkers that predict which patients with early stage breast cancer would benefit from more aggressive treatments would represent major advances within the breast cancer community. A need thus exists for clinical tests that can assist oncologists in making patient-specific treatment decisions.

BRIEF SUMMARY

In one aspect, a method of identifying a female patient with DCIS or early stage breast cancer who is likely to recur or progress to metastatic disease comprises
  providing a breast tumor sample from the female patient;
  determining the expression level of ASIP in the breast tumor sample to provide a test ASIP expression level;
  comparing the test ASIP expression levels to a reference ASIP expression level that is indicative of a likely progression to metastatic disease; and
  determining that the female patient is likely to progress to metastatic disease when the test ASIP expression level is equal to or greater than the reference ASIP expression level.

In another aspect a method of treating a female patient with DCIS or early stage breast cancer comprises
  providing a breast tumor sample from the female patient;
  determining the expression level of ASIP in the breast tumor sample to provide a test ASIP expression level;
  comparing the test ASIP expression level to a reference ASIP expression level that is indicative of a likely progression to metastatic disease; and
  administering aggressive breast cancer treatment when it is determined that the female patient is likely to progress to metastatic disease when the test ASIP expression level is equal to or greater than the reference ASIP expression level.

The above-described and other features will be appreciated and understood by those skilled in the art from the following detailed description, drawings, and appended claims.

DETAILED DESCRIPTION

It has been found that the level of expression of Agouti Signaling Protein (ASIP) mRNA is inversely correlated with time to progression of early stage breast cancer to metastatic disease; the subset of patients whose cancer expressed the highest level of ASIP mRNA exhibited progression faster and more frequently than the subsets that expressed intermediate or lowest levels of ASIP mRNA. Without being held to theory, it is believed that ASIP acts within the breast as an autocrine or paracrine suppressor of the melanocortin signaling network (MSN). ASIP, in addition to certain other MSN genes, thus serves as a prognostic and predictive biomarker for the progression of breast cancer.

Figure 1:
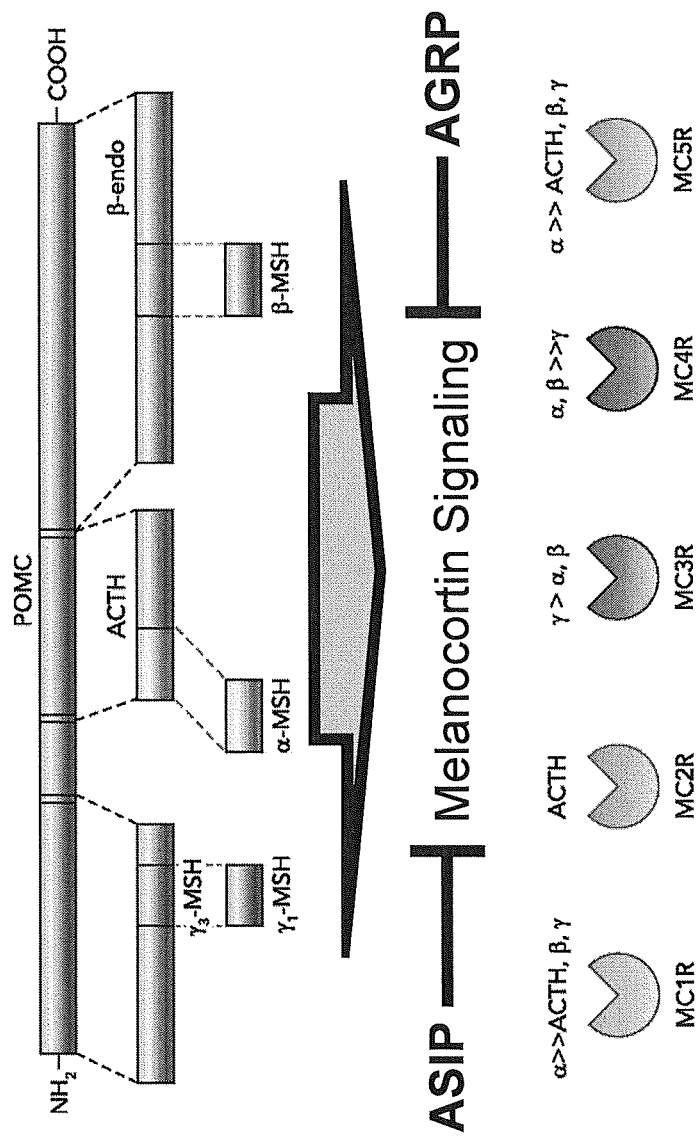
FIG. 1 is a schematic of the melanocortin signaling network.

The MSN is comprised of the melanocortins, a family of related peptide hormones, e.g., alpha-melanocyte stimulating hormone (αMSH) and adrenocorticotrophic hormone (ACTH), that are generated by post-translational processing of proopiomelanocortin (POMC); five distinct melanocortin receptor subtypes, designated MC1R through MC5R; and two endogenous antagonists/inverse agonists, ASIP and the homologous protein Agouti Related Neuropeptide (AGRP) (FIG. 1). The melanocortins regulate a diverse assortment of biological processes, including melanogenesis, glucocorticoid production, feeding behavior, efficiency of energy utilization, lipid metabolism, inflammation and macrophage function. Each of the distinct melanocortin peptides binds to and activates one or more of the 5 melanocortin receptor types, all of which are seven transmembrane, G protein coupled, receptors that signal through activation of adenylate cyclase and generation of 3',5'-cyclic adenosine monophosphate (cAMP). ASIP functions as an autocrine or paracrine antagonist or inverse agonist for the different melanocortin receptor types, thereby inhibiting signaling induced by the melanocortin ligands (antagonism) or independently reducing adenylate cyclase activity (inverse agonism). Expression of ASIP and the different melanocortin receptor types is cell type specific. For example, ASIP produced within the skin acts on MC1R expressed on melanocytes to block the induction of melanogenesis by αMSH, thereby influencing skin and hair color in multiple mammalian species, including mouse, rat and human. In the brain, ASIP acts on MC4R expressed on specific hypothalamic neurons to stimulate feeding behavior and thereby contributes to obesity. The function of the MSN in normal or neoplastic mammary gland has not been established in any species.

ASIP resides in the region of human chromosome 20q11.22 that has been associated with breast cancer in two independent genome-wide association studies (GWASs). In the first study, single nucleotide polymorphism (SNP) rs2284378 was associated with breast cancer and most strongly associated with estrogen receptor-alpha (ESR1)-negative breast cancer. In the second study, SNP rs6142050 was associated with triple negative breast cancer. The 20q11.22 breast cancer risk locus harbors ASIP and two additional genes: RALY, which encodes a heterogeneous nuclear ribonucleoprotein, and EIF2S2, which encodes eukaryotic translation initiation factor 2, subunit 2 beta. Neither the functionally significant genetic variant within this 20q11.22 locus nor the gene(s) upon which it acts to influence breast cancer development is presently known. Interestingly, the 20q11.22 breast cancer associated SNPs are in linkage disequilibrium (LD) with two SNPs (rs1015362 and rs4911414) that have been associated with skin, hair and eye color, freckling, sensitivity to sunburn and susceptibility to melanoma and basal cell carcinoma of the skin. The skin coloration/cancer phenotypes are conferred through actions of a regulatory variant(s) on ASIP. Therefore, co-localization of the skin coloration/cancer SNPs with the breast cancer SNPs upstream of ASIP lends support to the hypothesis that ASIP may confer the actions of the breast cancer risk variants mapped to 20q11.22.

In one embodiment, a method of identifying a female patient with DCIS or early stage breast cancer who is likely to progress to metastatic disease comprises providing a breast tumor sample from the female patient; determining the expression level of ASIP mRNA and/or protein in the breast tumor sample to provide a test ASIP expression level; comparing the test ASIP expression levels to a reference ASIP expression level that is indicative of a likely progression to metastatic disease; and determining that the female patient is likely to progress to metastatic disease when the test ASIP expression level is equal to or greater than the reference ASIP expression level.

Thus, described herein is a prognostic and predictive test for determining the likelihood of a female patient with early stage breast cancer developing metastatic breast cancer as well as methods of treating the patients based upon the test results. While tamoxifen has some efficacy in the treatment of breast cancer, its efficacy in women with a high risk of metastatic disease may be limited, leading to the suggestion that in women with a high risk of metastatic disease, tamoxifen should be used in combination therapy with other agents. It would be very helpful to identify women with a high risk of developing metastatic breast cancer to use more aggressive therapies, while avoiding the use of aggressive therapies in women at a lower risk of developing metastatic breast cancer.

The correlation between high ASIP mRNA expression and rapid progression to metastasis was strong in patients that had not been treated with tamoxifen prior to providing a tumor sample. Thus, in one embodiment, the female patient has not been treated with tamoxifen prior to obtaining the breast tumor sample.

The term "prognosis" is used herein to refer to the prediction of the likelihood of cancer-attributable death or progression, including development of metastatic breast cancer. The term "prediction" is used herein to refer to the likelihood that a patient will respond either favorably or unfavorably to a drug or set of drugs.

Exemplary patients are female patients with ductal carcinoma in situ (DCIS) or early stage breast cancer. As used herein, DCIS (or Stage 0 breast cancer), often considered to be the earliest form of breast cancer, is the presence of abnormal cells inside of a milk duct of the breast. Early stage breast cancer refers to Stage I, II (A or B), and III A breast cancer, which include cancers that have spread to the regional lymph nodes, but not cancers that have spread to more distant lymph nodes or other parts of the body. Stage I breast cancers, for example, are confined only to the area where abnormal cells first began to develop and are smaller than 2 cm in diameter. Stage IA cancers have not spread to the lymph nodes, while in stage IB, the lymph nodes have evidence of cancer. Stage II breast cancers are either larger than two centimeters or have spread to the axillary lymph nodes. In stage III breast cancer, cancer has spread from the immediate region of the tumor to invade lymph nodes and muscles, but has not spread to distant organs. Metastatic breast cancer, or stage IV breast cancer, is breast cancer that has spread to other parts of the body such as the lungs, liver, bones, or brain.

The term "tumor," as used herein, refers to all neoplastic cell growth and proliferation, whether malignant or benign, and all pre-cancerous and cancerous cells and tissues. The term "(lymph) node negative" cancer, such as "(lymph) node negative" breast cancer, is used herein to refer to cancer that has not spread to the lymph nodes. The term "estrogen receptor positive tumor" (ER+) refers to a tumor that has wherein at least 1% of the cells in the sample tested have estrogen receptors. The term ER+ or ESR1+ generally refers to estrogen receptor alpha (official symbol ESR1). Estrogen receptor beta is ESR2. Identification of cells with estrogen receptors is done using immunohistological methods that are well-known in the art. The term "luminal B tumor" refers to a subtype of breast cancers generally defined as estrogen receptor positive tumors that exhibit varying levels of progesterone receptor and ERRB2 (also known as HER2), as well as a high proliferative index. Identification of cells with progestone receptors is done using immunohistological methods, and identification of HER2 positive cells (i.e., HER2 overexpressing) is done using immunohistological methods or fluorescence in situ hybridization. More recently, a PAM50 gene expression assay has been used to identify breast cancer subtypes, including luminal B tumors, for example (See U.S. Pat. No. 9,181,588 for a description of the PAM50 assay).

The correlation with high ASIP gene expression and rapid progression to metastasis was strongest in those patients whose tumors were classified at diagnosis as luminal B, estrogen receptor positive, or lymph node negative. Thus, in one embodiment, the breast tumor sample is determined to be a luminal B tumor, an estrogen receptor positive tumor, or a lymph node negative tumor.

The disclosed methods can further include determining the expression level of one or more of proopiomelanocortin, MC1R, MC2R, MCR3, MC4R, MC5R, and AGRP in the breast tumor sample to provide a test ASIP, proopiomelanocortin, MC1R, MC2R, MCR3, MC4R, MC5R, or AGRP expression level. The method can also include comparing the test proopiomelanocortin, MC1R, MC2R, MCR3, MC4R, MC5R, or AGRP expression levels to reference proopiomelanocortin, MC1R, MC2R, MCR3, MC4R, MC5R, or AGRP expression levels that are indicative of a likely progression to metastatic disease; and determining that the female patient is likely to progress to metastatic disease when the test ASIP and proopiomelanocortin, MC1R, MC2R, MCR3, MC4R, MC5R, or AGRP expression level is equal to or greater than the reference ASIP and proopiomelanocortin, MC1R, MC2R, MCR3, MC4R, MC5R, or AGRP expression level.

The term "expression level" includes methods of quantification of the amount of a biomarker in a sample such as mRNA levels, protein levels, or cellular markers for the gene of interest.

Included herein are assays to measure the levels of specified genes (mRNAs) or their expression products (proteins) in a biological sample comprising cancer cells. Exemplary biological samples are fresh or archived tissue samples obtained from a tumor, e.g., by tumor biopsy or aspiration, but biological fluids containing tumor cells can also be used in the analysis. In one embodiment, determining expression levels involves the determination of mRNA levels in a tissue sample, such as a frozen biopsy specimen or a fixed, paraffin-embedded tumor biopsy specimen that has already been collected from the patient and archived. Thus, the test can be completely non-invasive. It is also compatible with several different methods of tumor tissue harvest, for example, core biopsy and fine needle aspiration. The tumor tissue can be, but does not need to be, grossly dissected away from normal tissue.

RNA isolation from a tissue sample can be performed using purification kit, buffer set and protease from commercial manufacturers, such as Qiagen, according to the manufacturer's instructions. For example, total RNA from cells can be isolated using Qiagen RNeasy® mini-columns. Other commercially available RNA isolation kits include MasterPure™ Complete DNA and RNA Purification Kit (EPICENTRE®, Madison, Wis.), and Paraffin Block RNA Isolation Kit (Ambion, Inc.). Total RNA from tissue samples can be isolated using RNAStat-60™ (Tel-Test). RNA prepared from tumor can be isolated, for example, by cesium chloride density gradient centrifugation.

Isolated mRNA can be amplified using PCR techniques that are well known in the art. Specific RNA species can be quantified using reverse transcription PCR techniques also well known in the art. Exemplary methods employ the Taq DNA polymerase, which has a 5'-3' nuclease activity but lacks a 3'-5' proofreading endonuclease activity. As an example, TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data. TaqMan® RT-PCR can be performed using commercially available systems.

The laboratory assay for gene expression can use a variety of different platforms. One embodiment for use with fixed paraffin-embedded tissues is quantitative reverse transcriptase polymerase chain reaction qRT-PCR. However, the other technology platforms including mass spectroscopy and DNA microarrays can also be used. In the case of DNA microarrays the polynucleotide probes can be cDNAs ("cDNA arrays") that are typically about 500 to 5000 bases long, although shorter or longer cDNAs can also be used. Alternatively, the polynucleotides can be oligonucleotides (DNA microarrays), which are typically about 20 to 80 bases long, although shorter and longer oligonucleotides are also suitable and are within the scope of the invention. The solid surface can, for example, be glass or nylon, or any other solid surface typically used in preparing arrays, such as microarrays, and is typically glass.

In another embodiment, in situ hybridization is used to determine the expression level of ASIP and other biomarkers as disclosed herein. In situ hybridization (ISH) is a method of localizing and detecting specific mRNA sequences in tissue sections or cell preparations by hybridizing the complementary strand of a nucleotide probe to the sequence of interest. ISH provides both temporal and spatial information about gene expression and genetic loci. ISH methods include fluorescence (FISH) and chromogenic (CISH) detection. Multiplexing fluorescence in situ hybridization (FISH) enables one to study multiple targets simultaneously and visualize co-localization within a single specimen. Using spectrally distinct fluorophore labels for each different hybridization probe, this approach allows the resolution of several genetic elements or multiple gene expression patterns in a single specimen, with multicolor visual display.

In yet another embodiment, determining the expression level of ASIP and other biomarkers comprises determining protein levels instead of mRNA levels. Protein levels can be determined using an interaction partner for the protein, which is an entity that physically associates with the markers such as an antibody that specifically binds the marker. The interaction partner optionally includes a detectable label.

In another embodiment, detection includes detection of a cell biomarker whose expression level is indicative of the expression level of the gene of interest, e.g., ASIP.

Table 1 provides identification information for ASIP and the MSN genes.

TABLE 1

ASIP and MSN markers

| Gene | Gene ID (NCBI) | Accession number | SEQ ID NO: |
|---|---|---|---|
| ASIP | 434 | NM_001672.2 | 1 |
| AGRP | 181 | NM_001138.1 | 2 |
| proopiomelano-cortin | 5443 | NM_001035256.2 | 3 |
| | | NM_000939.3 | 4 |
| | | NM_001319204.1 | 5 |
| | | NM_001319205.1 | 6 |
| MC1R | 4157 | NM_002386.3 | 7 |
| MC2R | 4158 | NM_000529.2 | 8 |
| | | NM_001291911.1 | 9 |
| MC3R | 4159 | NM_019888.3 | 10 |
| MC4R | 4160 | NM_005912.2 | 11 |
| MC5R | 4161 | NM_005913.2 | 12 |

The test ASIP, proopiomelanocortin, MC1R, MC2R, MC3R, MC4R, MC5R, or AGRP expression level is compared to a reference ASIP, proopiomelanocortin, MC1R, MC2R, MC4R, MC5R, or AGRP expression level that is indicative of a likely progression to metastatic disease. For example, expression of a marker such as ASIP can be compared to reference standard values obtained in study of a large cohort of breast cancers. High expression would mean level of expression relative to the large breast cancer cohort, e.g., top 10%, 25%, 33%, and the like.

In another embodiment, an exemplary predictive algorithm provides a score for a patient sample such as a recurrence score, a response to treatment score, a DCIS score, a metastasis score, or an expression score, for example. The lower the Recurrence Score or DCIS Score, for example, the lower the chances are that a woman's breast cancer will come back; the higher the Recurrence or DCIS Score, the greater the chances that breast cancer will come back. The lower the Recurrence Score result is, the less likely a woman is to benefit from chemotherapy, and the higher the Recurrence Score result, the more likely she is to benefit from chemotherapy. The metastasis score is a measure of the likelihood of a woman developing metastatic breast cancer. An expression score can be used to determine the risk of progression of early stage breast cancer to metastatic disease. In calculating a score for a sample, the expression level of a gene in a panel of genes can be weighted by a multiplication factor as provided in Table 2. Exemplary primers for mRNA amplification can be found in U.S. Pat. No. 7,526,387, incorporated herewith by reference for its disclosure of mRNA markers for breast cancer and primers suitable for identifying their level of expression.

TABLE 2

Oncotype DX ® markers and multiplication factors.

| Gene | Accession Number | SEQ ID NO: | Weighting factor |
|---|---|---|---|
| MKI67 | NM_002417 | 13 | +1.04 |
| AURKA (STK15) | NM_003600 | 14 | +1.04 |
| BIRC5 | NM_001168 | 15 | +1.04 |
| CCNB1 | NM_031966 | 16 | +1.04 |
| MYBL2 | NM_002466 | 17 | +1.04 |

TABLE 2-continued

Oncotype DX ® markers and multiplication factors.

| Gene | Accession Number | SEQ ID NO: | Weighting factor |
|---|---|---|---|
| GRB7 | NM_005310 | 18 | +0.47 |
| ERBB2 | NM_001982 | 19 | +0.47 |
| MMP11 (STMY3) | NM_005940 | 20 | +0.10 |
| CTSV (CTSL2) | NM_001333 | 21 | +0.10 |
| BAG1 | NM_004323 | 22 | +0.7 |
| CD68 | NM_001251 | 23 | +0.05 |
| ESR1 (EstR1) | NM_000125 | 24 | −0.34 |
| PGR (PR) | NM_000926 | 25 | −0.34 |
| BCL2 | NM_000633 | 26 | −0.34 |
| SCUBE2 (CEGP1) | NM_020974 | 27 | −0.34 |
| GSTM1 | NM_000561 | 28 | −0.08 |
| GAPDH | NM_002046 | 29 | normalization |
| RPLP0 | NM_001002 | 30 | normalization |
| GUSB (GUS) | NM_000181 | 31 | normalization |
| TFRC | NM_003234 | 32 | normalization |
| ACTB(B-actin) | NM_001101 | 33 | normalization |

Figure 4:
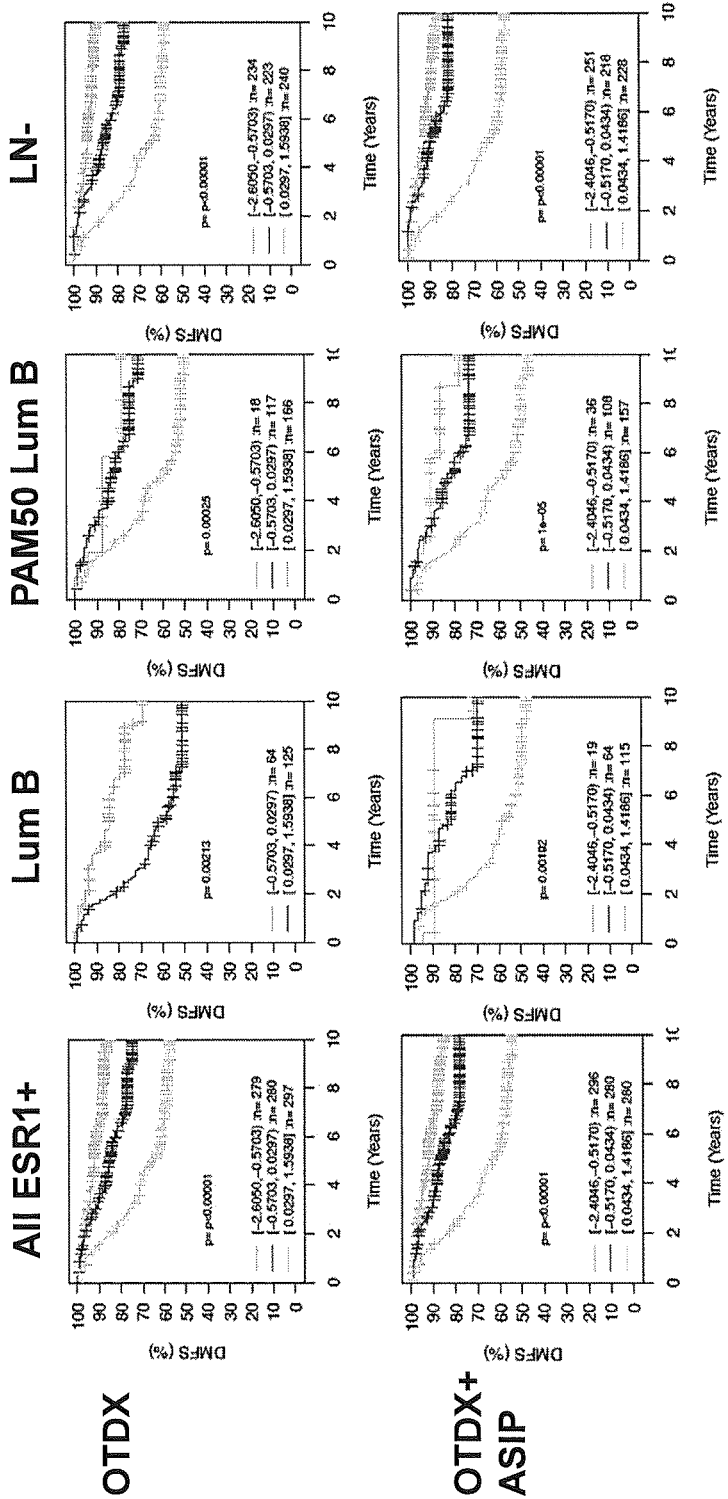
FIG. 4 shows that the addition of ASIP to the OncoType DX® gene panel strengthens the statistical association between weighted expression of the OncoType DX® gene panel and progression to metastatic breast cancer in early stage ESR1 positive breast cancer patients whose tumors were classified within the Luminal B, PAM50 Luminal B and lymph node negative subsets using established criteria well defined in the art.
Figure 5:
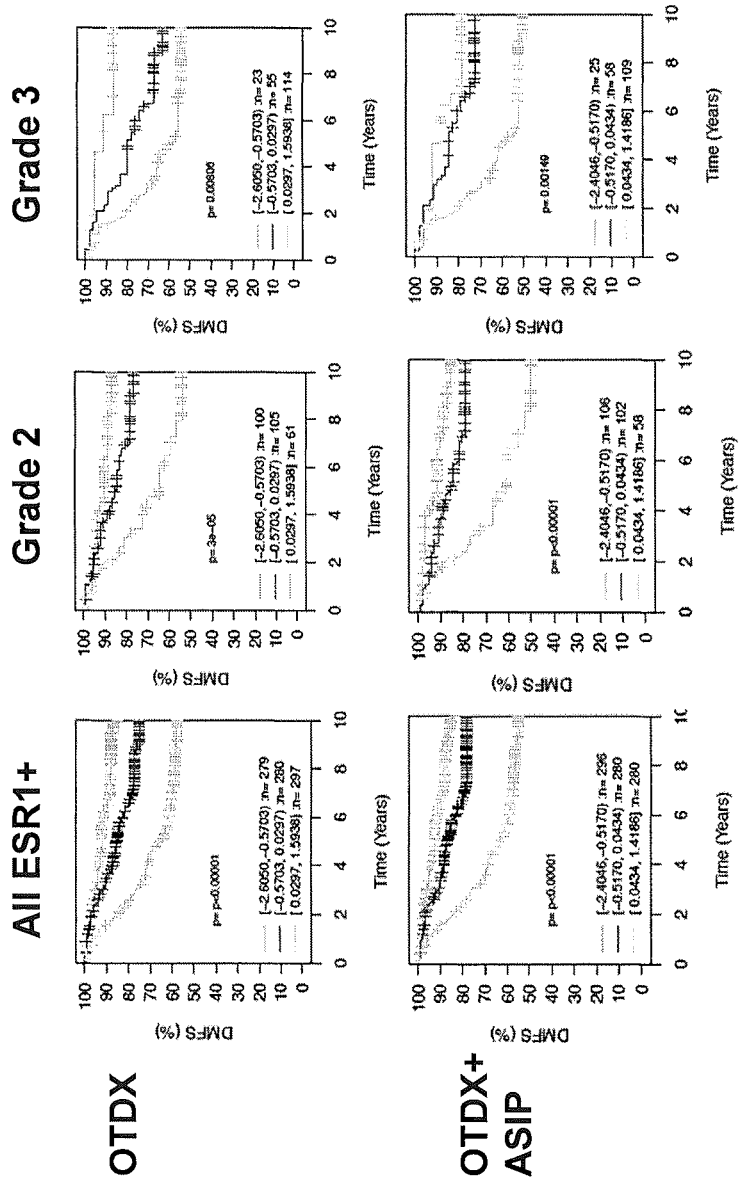
FIG. 5 shows that the addition of ASIP to the OncoType DX® gene panel strengthens the statistical association between weighted expression of the OncoType DX® gene panel and progression to metastatic breast cancer in early stage ESR1 positive breast cancer patients whose tumors were classified as Grade 2 or Grade 3 using established criteria well defined in the art.

The Oncotype DX® test uses the expression levels and weighting factors of the genes from Table 2 to calculate a recurrence score for a tumor sample. It has been found that adding ASIP expression, assuming a weighting factor of +1.04, enhances the ability of the test to predict which early stage cancers are likely to progress to metastatic disease, with or without treatment with tamoxifen. (See, FIGS. 4-6)

Thus, in one aspect, the method further comprises determining a gene expression level of one or more markers from Table 2 such as the proliferation markers MKI67, AURKA, BIRC5, CCNB1 or MYBL2 in the breast tumor sample from the female patient to provide a test Table 2 marker expression level, comparing the test Table 2 marker expression level to a reference Table 2 marker expression level that is indicative of a likely progression to metastatic disease, and determining that the female patient is likely to progress to metastatic disease when the test ASIP expression level is equal to or greater than the reference ASIP expression level and the test Table 2 marker expression level is equal to or greater than the reference Table 2 marker expression level. In one aspect, gene expression levels of all of the Table 2 markers are determined.

An exemplary predictive algorithm is an expression signature of the breast tumor sample. The expression of one or more of ASIP, proopiomelanocortin, MC1R, MC2R, MC3R, MC4R, MC5R, or AGRP may be determined using methods known in the art and described herein, and normalized to control housekeeping genes. Optionally, the gene expression can be also normalized to a control sample by determining the ratio of the expression level of each gene between the sample and a control sample. While any control sample known in the art may be utilized, one exemplary control sample comprises in vitro transcribed RNA sequences of each gene at a known concentration. The mean of all the log ratios or normalized values of each gene can be calculated to determine the average gene expression of the sample. The proliferation signature can be determined by scaling the calculated average gene expression to a range of, for example 1-10, wherein the scaling is determined by a reference sample set. The lowest value of the expression signature corresponds to the lowest expression signature in the reference sample set, and the highest value of the expression signature corresponds to the highest expression signature, and the expression signature of a sample can be determined through linear interpolation between the highest and lowest values of the reference sample set.

In this embodiment, the reference sample set is a population of breast cancer samples wherein the expression signature of each sample has been determined. The reference sample set must be of sufficient size such that the set can be used to assess various clinical variables, for example response to treatment regimen, estrogen receptor status, and tumor size and the like, with statistical significance. In some embodiments, the reference sample set comprises primary breast cancer tissue from subjects diagnosed with breast cancer and "normal" breast tissue samples from reduction mammoplasties or non-cancerous breast tissue. These samples can be classified to particular breast cancer intrinsic subtypes, for example Luminal A, Luminal B, Basal-like and Her2. For example, the reference sample set contains at least 100 samples, at least 200 samples, at least 300 samples, at least 400 samples, at least 500 samples, at least 600 samples, at least 700 samples, at least 800 samples, at least 900 samples, or at least 1000 samples.

The expression signatures of each reference sample in the reference sample set can be arranged from lowest to highest, for example 1 to 10. Once arranged by expression signature, the reference sample set can then be divided into sub-ranges, wherein each sub-range is a non-overlapping fraction of the reference set. The expression signature of the sample can be compared to reference sample set. These sub-ranges are used to determine the cutoff threshold limits for a low expression signature. For example, the sub-range can be 50%, 33%, 30%, 25%, 20%, 15%, 10%, or 5% of the expression signatures of the arranged reference sample set. Irrespective of the number of sub-ranges, the expression signature of the sample is deemed to be a low expression signature if it is present within the lowest sub-range of the reference sample set. For example, if the reference sample set is divided into three sub-ranges, the classification of a low expression signature is assigned if the expression signature of the sample is present within the lowest 33% of expression scores of the arranged reference sample set.

Exemplary primers for mRNA amplification can be found in U.S. Publication No. 2011/0145176, incorporated herewith by reference for its disclosure of mRNA markers for breast cancer and primers suitable for identifying their level of expression.

TABLE 3

| PAM50 | | |
|---|---|---|
| Sequence name | Identifier | SEQ ID NO: |
| ACTR3B | NM_020445 | 34 |
|  | NM_001040135 | 35 |
| ANLN | NM_018685 | 36 |
| BAG1 | NM_004323 | 37 |
| BCL2 | NM_000633 | 38 |
| BIRC5 | NM_001012271 | 39 |
| BLVRA | BX647539 | 40 |
| CCNB1 | NM_031966 | 41 |
| CCNE1 | BC035498 | 42 |
| CDC20 | BG256659 | 43 |
| CDC6 | NM_001254 | 44 |
| CDCA1 (NUF2) | NM_031423 | 45 |
| CDH3 | BC041846 | 46 |
| CENPF | NM_016343 | 47 |
| CEP55 | AB091343 | 48 |
| CXXC5 | BC006428 | 49 |
| EGFR | NM_005228 | 50 |
| ERBB2 | NM_001005862 | 51 |
| ESR1 | NM_001122742 | 52 |
| EXO1 | NM_130398 | 53 |

TABLE 3-continued

| PAM50 | | |
|---|---|---|
| Sequence name | Identifier | SEQ ID NO: |
| FGFR4 | AB209631 | 54 |
| FOXA1 | NM_004496 | 55 |
| FOXC1 | NM_001453 | 56 |
| GPR160 | AJ249248 | 57 |
| GRB7 | NM_005310 | 58 |
| HSPC150 (UBE2T) | NM_014176 | 59 |
| KIF2C | NM_006845 | 60 |
| KNTC2 (NDC80) | NM_006101 | 61 |
| KRT14 | BC042437 | 62 |
| KRT17 | AK095281 | 63 |
| KRT5 | M21389 | 64 |
| MAPT | NM_001123066 | 65 |
| MDM2 | M92424 | 66 |
| MELK | NM_014791 | 67 |
| MIA | BG765502 | 68 |
| MKI67 | NM_002417 | 69 |
| MLPH | NM_024101 | 70 |
| MMP11 | NM_005940 | 71 |
| MYBL2 | BX647151 | 72 |
| MYC | NM_002467 | 73 |
| NAT1 | BC013732 | 74 |
| ORC6L | NM_014321 | 75 |
| PGR | NM_000926 | 76 |
| PHGDH | AK093306 | 77 |
| PTTG1 | BE904476 | 78 |
| RRM2 | AK123010 | 79 |
| SFRP1 | BC036503 | 80 |
| SLC39A6 | NM_012319 | 81 |
| TMEM45B | AK098106 | 82 |
| TYMS | BQ056428 | 83 |
| UBE2C | BC032677 | 84 |

The PAM50 test uses the gene expression levels of 50 genes to classify breast cancer subtypes. Adding ASIP or MSN genes proopiomelanocortin, MC1R, MC2R, MC3R, MC4R, MC5R, and AGRP expression levels to the PAM50 assay, or a subset of the markers therein, is expected to improve the predictability of the method.

Thus, in one embodiment, the method further comprises determining a gene expression level of one or more markers from Table 3 such as CDC20, CEP55, MKI67, RRM2 or UBE2C in the breast tumor sample from the female patient to provide a test Table 3 marker expression level, comparing the test Table 3 marker expression level to a reference Table 3 marker expression level that is indicative of a likely progression to metastatic disease, and determining that the female patient is likely to progress to metastatic disease when the test ASIP expression level is equal to or greater than the reference ASIP expression level and the test Table 3 marker expression level is equal to or greater than the reference Table 3 marker expression level.

A method of determining a tumor-related status of an individual comprises the determining a difference in transcript levels, or lack thereof, between a target and standard or control, wherein the difference, or lack thereof, determines the individual's tumor-related status. In a more specific embodiment, the standard or control molecules comprise marker-derived polynucleotides from a pool of samples from normal individuals, or a pool of tumor samples from individuals having sporadic-type tumors. In an embodiment, the standard or control is an artificially-generated pool of marker-derived polynucleotides, which pool is designed to mimic the level of marker expression exhibited by clinical samples of normal or breast cancer tumor tissue having a particular clinical indication (i.e., cancerous or non-cancerous; ER(+) or ER(−) tumor; BRCA1—or sporadic type tumor). In another embodiment, the control molecules comprise a pool derived from normal or breast cancer cell lines.

Thus, the level of polynucleotides (i.e., mRNA or polynucleotides derived therefrom) in a sample from an individual, expressed from the markers provided in Table 4 can be compared to the level of expression of the same markers from a control, wherein the control comprises marker-related polynucleotides derived from ER(+) samples, ER(−) samples, or both. In an embodiment, the comparison is to both ER(+) and ER(−), such as a comparison to polynucleotide pools from a number of ER(+) and ER(−) samples, respectively. Where the individual's marker expression most closely resembles or correlates with the ER(+) control, and does not resemble or correlate with the ER(−) control, the individual is classified as ER(+). Where the pool is not pure ER(+) or ER(−), for example, a sporadic pool may be used. A set of experiments using individuals with known ER status can be hybridized against the pool, in order to define the expression templates for the ER(+) and ER(−) group. Each individual with unknown ER status is hybridized against the same pool and the expression profile is compared to the templates (s) to determine the individual's ER status.

The similarity between the marker expression profile of an individual and that of a control can be assessed a number of ways. In the simplest case, the profiles can be compared visually in a printout of expression difference data. Alternatively, the similarity can be calculated mathematically as described in U.S. Pat. No. 7,863,001, incorporated herein by reference for its disclosure of marker genes and mathematical calculations of similarities of expression profiles.

TABLE 4

MammaPrint markers

| GeneName | GeneID | GeneDescription | SEQ ID NO. |
|---|---|---|---|
| BBC3 | 27113 | BCL2 binding component 3 | 85 |
| EGLN1 | 54583 | egl-9 family hypoxia-inducible factor 1 | 86 |
| TGFB3 | 7043 | transforming growth factor beta 3 | 87 |
| ESM1 | 11082 | endothelial cell specific molecule 1 | 88 |
| IGFBP5 | 3488 | insulin like growth factor binding protein 5 | 89 |
| FGF18 | 8817 | fibroblast growth factor 18 | 90 |
| SCUBE2 | 57758 | signal peptide, CUB domain and EGF like domain containing 2 | 91 |
| WISP1 | 8840 | WNT1 inducible signaling pathway protein 1 | 92 |
| FLT1 | 2321 | fms related tyrosine kinase 1 | 93 |
| HRASLS | 57110 | HRAS like suppressor | 94 |
| STK32B | 55351 | serine/threonine kinase 32B | 95 |
| RASSF7 | 8045 | Ras association domain family member 7 | 96 |
| DCK | 1633 | deoxycytidine kinase | 97 |
| MELK | 9833 | maternal embryonic leucine zipper kinase | 98 |
| EXT1 | 2131 | exostosin glycosyltransferase 1 | 99 |
| GNAZ | 2781 | G protein subunit alpha z | 100 |
| EBF4 | 57593 | early B cell factor 4 | 101 |
| MTDH | 92140 | metadherin | 102 |

TABLE 4-continued

MammaPrint markers

| GeneName | GeneID | GeneDescription | SEQ ID NO. |
|---|---|---|---|
| PITRM1 | 10531 | pitrilysin metallopeptidase 1 | 103 |
| QSOX2 | 169714 | quiescin sulfhydryl oxidase 2 | 104 |
| CCNE2 | 9134 | cyclin E2 | 105 |
| ECT2 | 1894 | epithelial cell transforming 2 | 106 |
| CENPA | 1058 | centromere protein A | 107 |
| LIN9 | 286826 | lin-9 DREAM MuvB core complex | 108 |
| NDC80 | 10403 | NDC80 kinetochore complex component | 109 |
| MCM6 | 4175 | minichromosome maintenance complex component | 110 |
| NUSAP1 | 51203 | nucleolar and spindle associated protein 1 | 111 |
| ORC6 | 23594 | origin recognition complex subunit 6 | 112 |
| TSPYL5 | 85453 | TSPY-like 5 | 113 |
| RUNDC1 | 712278 | RUN domain containing 1 | 114 |
| PRC1 | 9055 | protein regulator of cytokinesis | 115 |
| RFC4 | 5984 | replication factor C subunit 4 | 116 |
| RECQL5 | 9400 | RecQ like helicase 5 | 117 |
| CDCA7 | 83879 | cell division cycle associated 7 | 118 |
| DTL | 51514 | denticleless E3 ubiquitin protein | 119 |
| COL4A2 | 1284 | collagen type IV alpha 2 | 120 |
| GPR180 | 160897 | G protein-coupled receptor 180 | 121 |
| MMP9 | 4318 | matrix metallopeptidase 9 | 122 |
| ADGFG6 | 57211 | adhesion G protein-coupled receptor | 123 |
| RTN4RL1 | 146760 | reticulon 4 receptor-like 1 | 124 |
| DIAPH3 | 81624 | diaphanous related formin 3 | 125 |
| CDC42BPA | 8476 | CDC42 binding protein kinase alpha | 126 |
| PALM2 | 114299 | paralemmin 2 | 127 |
| ALDH4A1 | 8659 | aldehyde dehydrogenase 4 family member A1 | 128 |
| LPCAT1 | 79888 | lysophosphatidylcholine acyltransferase 1 | 129 |
| OXCT1 | 5019 | 3-oxoacid CoA-transferase 1 | 130 |
| ECI2 | 10455 | enoyl-CoA delta isomerase | 131 |
| GMPS | 8833 | guanine monophosphate synthase | 132 |
| GSTM3 | 2947 | glutathione S-transferase mu 3 | 133 |
| SLC2A3 | 6515 | solute carrier family 2 member 3 | 134 |
| LOC100288906 | | hypothetical protein-withdrawn from NCBI | 135 |
| MSANTD3 | 91283 | Myb/SANT DNA binding domain containing 3 | 136 |
| ZNF385B | 151126 | zinc finger protein 385B | 137 |
| CMC2 | 56942 | C-x(9)-C motif containing 2 | 138 |
| SERF1A | 8293 | small EDRK-rich factor 1A | 139 |
| TMEM74B | 55321 | transmembrane protein 74B | 140 |

TABLE 4-continued

MammaPrint markers

| GeneName | GeneID | GeneDescription | SEQ ID NO. |
|---|---|---|---|
| LOC730018 | | withdrawn | 141 |
| LOC100131053 | | uncharacterized | 142 |
| AA555029_RC | | | 143 |
| DHX58 | 79132 | DEHX-box helicase 58 | 144 |
| NMU | 10874 | neuromedin U | 145 |
| UCHL5 | 51377 | ubiquitin C-terminal hydrolase L5 | 146 |
| KDM7A | 80853 | lysine demethylase | 147 |
| AP2B1 | 163 | adaptor related protein complex 2 beta 1 | 148 |
| MS4A7 | 58475 | ms4a7 | 149 |
| RAB6B | 51560 | RAB6B, member RAS oncogene family | 150 |
| EXOC7 | 23265 | exocyst complex component 7 | 151 |
| AKAP2 | 11217 | A-kinase anchoring protein 2 | 152 |

The MammaPrint test uses the gene expression levels of 70 genes to classify breast cancer subtypes. Adding ASIP or MSN gene proopiomelanocortin, MC1R, MC2R, MC3R, MC4R, MC5R, and AGRP expression levels to the MammaPrint assay, or a subset of the markers therein, is expected to improve the predictability of the method.

Thus, in one embodiment, the method further comprises determining a gene expression level of one or more markers from Table 4 in the breast tumor sample from the female patient to provide a test Table 4 marker expression level, comparing the test Table 4 marker expression level to a reference Table 4 marker expression level that is indicative of a likely progression to metastatic disease, and determining that the female patient is likely to progress to metastatic disease when the test ASIP expression level is equal to or greater than the reference ASIP expression level and the test Table 4 marker expression level is equal to or greater than the reference Table 4 marker expression level.

Tumor markers for breast cancer include SLC7A5, HTF9C, P53, NDRG1, and CEACAM5. Tumor markers can be identified in samples using interaction partners which are entities that physically associate with selected tumor markers. Thus, an entity that binds detectably to a tumor marker may be utilized as an interaction partner, so long as it binds with an appropriate combination of affinity and specificity.

Exemplary interaction partners are antibodies, or fragments (e.g., F(ab') fragments, F(ab')$_2$ fragments, Fv fragments, or sFv fragments) as are well-known in the art. Chimeric antibodies may be used as interaction partners, e.g., "humanized" antibodies. Antibody mimics such as small molecules and peptides may also be employed.

Association between an interaction partner and its cognate tumor marker can be detected by adding a detectable label to the interaction partner. Once a labeled interaction partner has bound a tumor marker, the complex may be visualized or detected in a variety of ways, with the particular manner of detection being chosen based on the particular detectable label, where representative detection means include, e.g., scintillation counting, autoradiography, measurement of paramagnetism, fluorescence measurement, light absorption measurement, measurement of light scattering and the like.

The results can be presented in a qualitative fashion. For example, a test report may indicate only whether or not a particular tumor marker was detected, perhaps also with an indication of the limits of detection. Additionally the test report may indicate the subcellular location of binding, e.g., nuclear versus cytoplasmic and/or the relative levels of binding in these different subcellular locations. The results may be presented in a semi-quantitative fashion. For example, various ranges may be defined and the ranges may be assigned a score (e.g., 0 to 5) that provides a certain degree of quantitative information. Such a score may reflect various factors, e.g., the number of cells in which the tumor marker is detected, the intensity of the signal (which may indicate the level of expression of the tumor marker), and the like. The results may be presented in a quantitative fashion, e.g., as a percentage of cells in which the tumor marker is detected, as a concentration, and the like. As will be appreciated by one of ordinary skill in the art, the type of output provided by a test will vary depending upon the technical limitations of the test and the biological significance associated with detection of the tumor marker. For example, in the case of certain tumor markers a purely qualitative output (e.g., whether or not the tumor marker is detected at a certain detection level) provides significant information. In other cases a more quantitative output (e.g., a ratio of the level of expression of the tumor marker in two samples) may be employed.

TABLE 5

Mammostrat markers

| Gene | Accession Number | SEQ ID NO: |
|---|---|---|
| SLC7A5 | NM_003486.6 | 153 |
| HTF9C (Trmt2a) | NM_022727.5 | 154 |
| P53 | AB082923.1 | 155 |
| NDRG1 | NM_001135242.1 | 156 |
| CEACAM5 | NM_004363.5 | 157 |

The Mammostrat test measures the levels of five certain genes in early-stage, hormone-receptor-positive breast cancer cells to help make treatment decisions based on whether the cancer has a lower or high risk of coming back (recurrence). Adding ASIP or MSN gene proopiomelanocortin, MC1R, MC2R, MC3R, MC4R, MC5R, and AGRP expression levels to the Mammostrat assay, or a subset of the markers therein, is expected to improve the predictability of the method.

Thus, in one embodiment, the method further comprises determining a gene expression level of one or more markers from Table 5 such as SLC7A5, HTF9C, P53, NDRG1, or CEACAM5 in the breast tumor sample from the female patient to provide a test Table 3 marker expression level, comparing the test Table 5 marker expression level to a reference Table 5 marker expression level that is indicative of a likely progression to metastatic disease, and determining that the female patient is likely to progress to metastatic disease when the test ASIP expression level is equal to or greater than the reference ASIP expression level and the test Table 5 marker expression level is equal to or greater than the reference Table 5 marker expression level.

The methods disclosed herein may also include classifying a breast tumor according to the likelihood of developing metastatic breast cancer.

If the risk of a particular patient developing metastatic disease is low, the physician might decide that chemotherapy following surgical removal of cancer, e.g. breast cancer is not necessary in order to ensure long term survival of patient. As a result, the patient will not be subjected to the often very severe side effects of standard of care chemotherapeutic treatment. Exemplary less toxic chemotherapeutic treatments include the use of Herceptin®. If, on the other hand, the risk of a particular patient developing metastatic disease is determined to be high, this information can be used to decide which chemotherapeutic or other treatment option (such as, radiation therapy) is most suitable for treating the patient. Similarly, if the risk of a particular patient developing metastatic disease is low, other, more effective, treatment modalities will be used to combat cancer in that particular patient.

If it is determined by the methods disclosed herein that a female patient is likely to progress to metastatic disease, the method further comprises administering aggressive breast cancer treatment. Aggressive breast cancer treatments include anthracycline and/or taxane-based treatment regimens or treatment with therapeutic drugs that are currently not part of the main line treatment protocol for a particular cancer, such as, for example, EGFR inhibitors, and/or by other treatment options, such as radiation therapy alone, or before or after chemotherapeutic treatment.

The invention is further illustrated by the following non-limiting examples.

EXAMPLES

Example 1: Data Mining of Gene Expression Data to Evaluate the Relationship Between Expression of ASIP and the MSN Genes and Clinical Outcomes of Breast Cancer The relationships between expression of specific genes at the mRNA level and progression of early stage breast cancers to metastatic disease were evaluated using publically available datasets and the online data mining tool GOBO: Gene Expression-Based Outcome for Breast Cancer Online. The datasets utilized in these analyses were generated using Affymetrix U133A oligonucleotide arrays and have been described in the art. These datasets were merged into a single dataset totaling 1881 samples as described in the art. The GOBO informatics tool accepts query inputs to be in the form of gene symbol, gene id number (NCBI) or Affymetrix probe id number. All queries were performed using gene id numbers. The GOBO tool evaluates associations between the level of expression of the gene of interest and selected clinical outcomes, including overall survival (OS), distant metastasis free survival (DMFS), relapse free survival (RFS) or mixed DMFS and RFS. All queries described herein were performed to evaluate associations between expression and DMFS.

Figure 2:
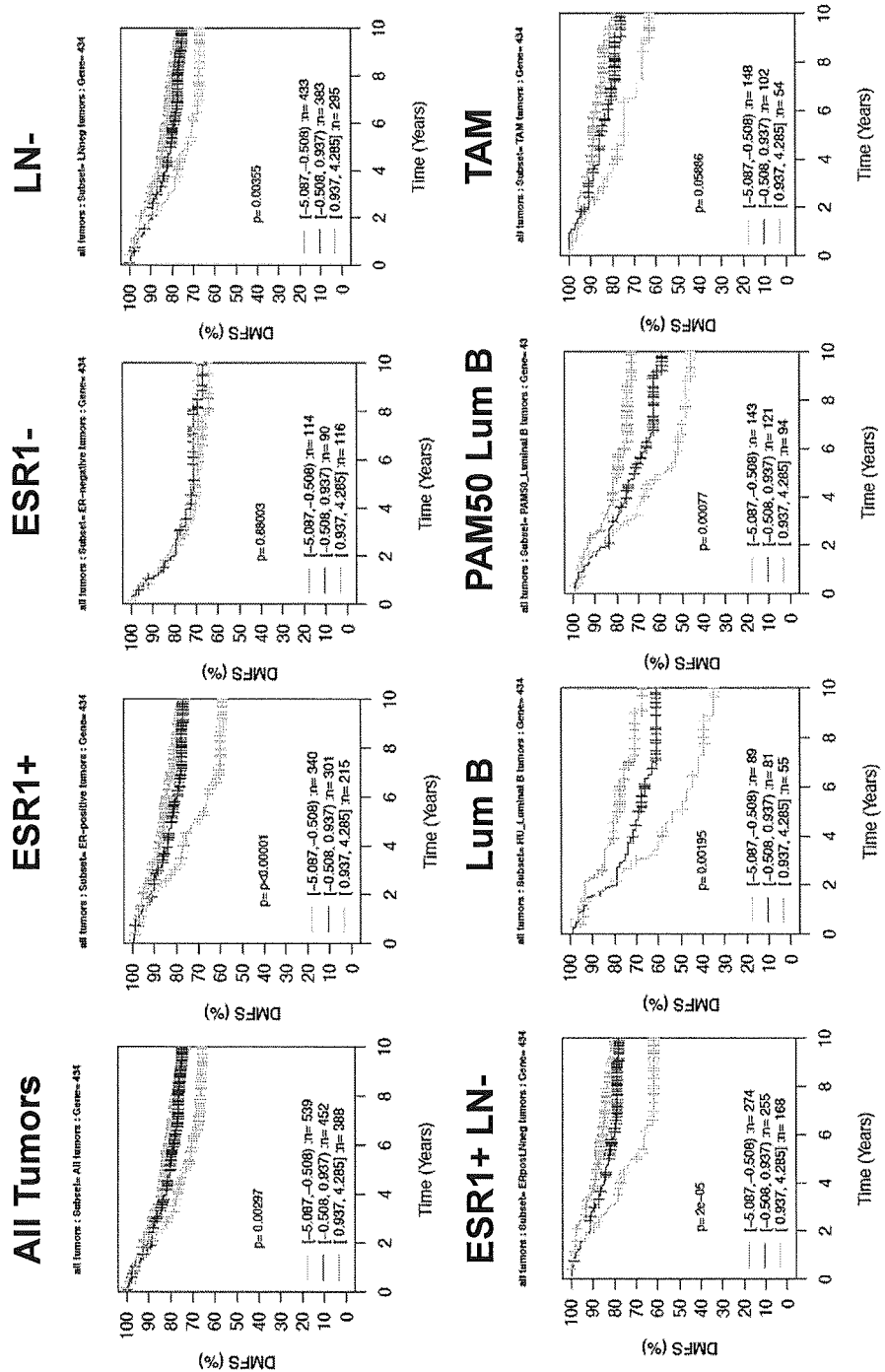
FIG. 2 shows the results of mining gene expression data for early stage breast cancer patients for the relationship between the expression of ASIP and clinical outcomes. The highest ASIP expression is associated with progression of early stage ESR1+ breast cancer to metastatic disease.

An initial query was performed to evaluate the relationship between the level of ASIP (gene id=434) expression and DMFS using the entire 1881 sample dataset (FIG. 2). GOBO was directed to divide the ASIP expression signal range into 3 quantiles, identify the number of patient samples falling into each of the 3 expression quantiles and calculate the statistical association with DMFS for the 3 groups of patient samples. This analysis revealed significant inverse correlations between ASIP expression and DMFS in the total patient sample set ($p=0.00297$) and in those patient samples classified as estrogen receptor positive (ESR1+, $p=0.00000373$), lymph node negative (LN−, $p=0.00355$), ESR1+LN− ($p=0.0000243$), luminal B (Lum B, $p=0.00195$), luminal B based on the PAM50 gene classifier (Prosigna®, Nanostring Technologies)(PAM50 Lum B, $p=0.00077$). No significant statistical relationship between ASIP expression and DMFS was observed in those patient samples classified as estrogen receptor negative (ESR1−). The relationship of high ASIP expression to DMFS in samples from patients treated with tamoxifen (TAM) following diagnosis approached statistical significance ($p=0.0588$).

Figure 3:
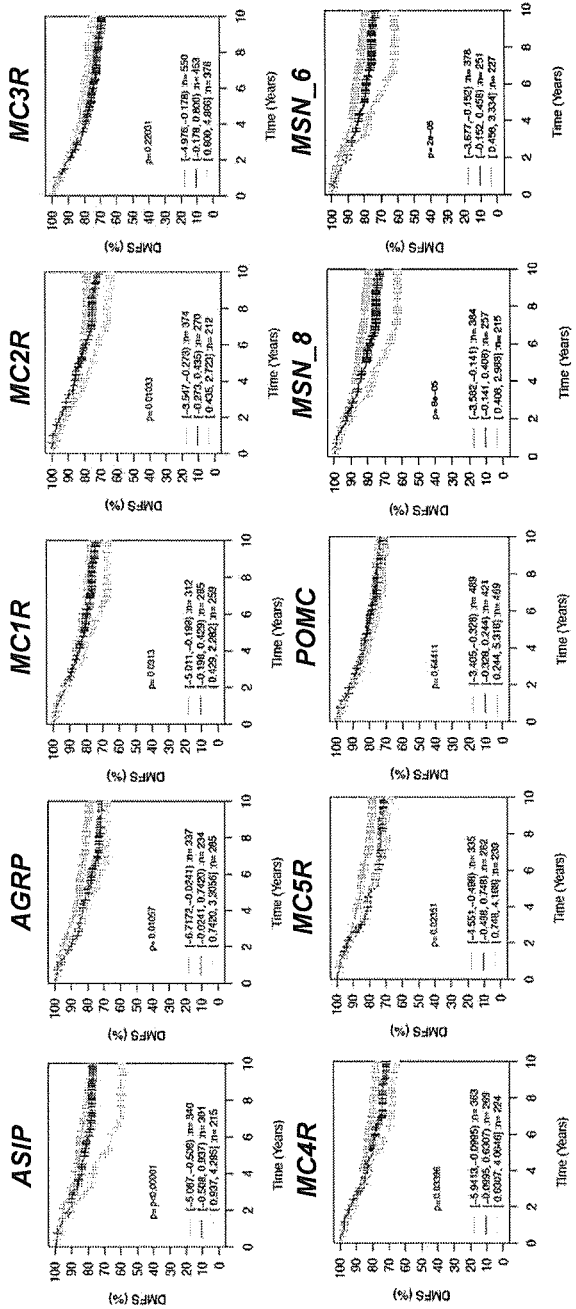
FIG. 3 shows results of mining gene expression data for early stage ESR1 positive breast cancer patients for the relationship between the expression of ASIP and the MSN genes and clinical outcomes. The highest expression of six melanocortin signaling network genes is associated with the progression of early stage ESR1+ breast cancer to metastatic disease.

A second set of analyses was performed to evaluate associations between expression of other melanocortin signaling network (MSN) genes and DMFS (FIG. 3). These analyses were restricted to the subset of patient samples classified as ESR1+, because this is the group in which high expression of ASIP was strongly correlated with DMFS. Significant inverse associations were observed for Agouti Related Neuropeptide (AGRP, $p=0.01056$), melanocortin 1 receptor (MC1R, $p=0.03130$), melanocortin 2 receptor (MC2R, $p=0.01033$), melanocortin 4 receptor (MC4R, $p=0.03396$) and melanocortin 5 receptor (MC5R, $p=0.02351$). No significant associations were observed between expression of melanocortin 3 receptor (MC3R, $p=0.54733$) or proopiomelanocortin (POMC, $p=0.28747$) and DMFS. Evaluation of these 8 MSN genes (MSN_8) as a gene set (equally weighted) yielded a highly significant inverse association ($p=8.14\times10^{-5}$) with DMFS. Similarly, evaluation of the 6 genes (MSN_6) that yielded significant individual inverse associations as a gene set yielded a highly significant inverse association ($p=2.11\times10^{-5}$) with DMFS (FIG. 3). Together, these observations indicate that ASIP and additional genes within the MSN have potential to serve as biomarkers for progression of early stage breast cancers.

Example 2: ASIP Improves the Predictive Power of OncoType DX®

Figure 6:
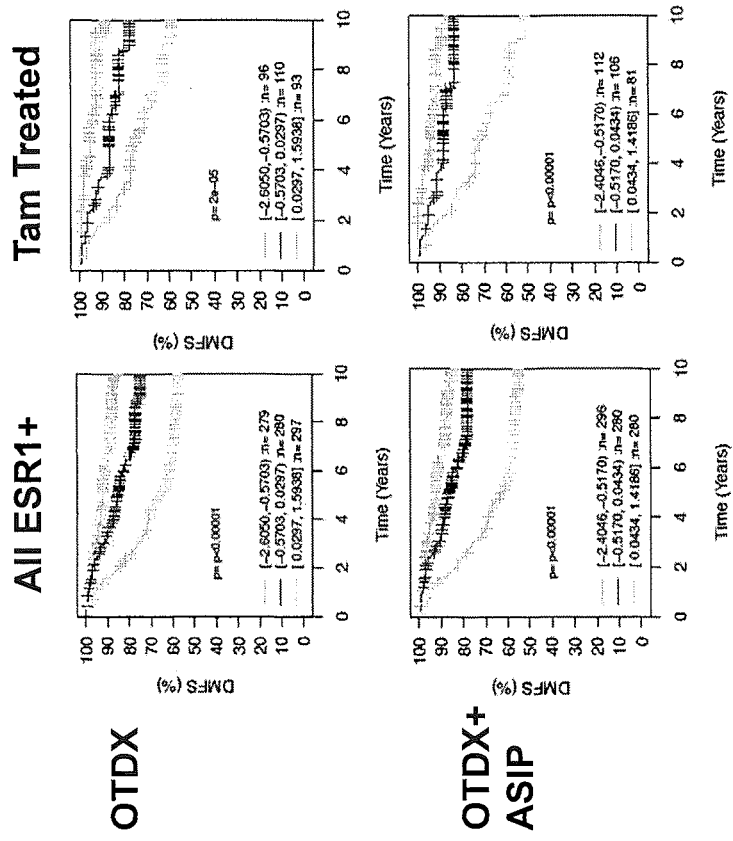
FIG. 6 shows that addition of ASIP to the OncoType DX® gene panel strengthens the statistical association between weighted expression of the OncoType DX® gene panel and progression to metastatic breast cancer in early stage ESR1 positive breast cancer patients who received tamoxifen as part of their treatment regimen.

OncoTypeDX® is an established tool for predicting progression of early stage breast cancers. Therefore, we evaluated the potential of ASIP to enhance the ability of the OncoTypeDX® gene set to predict progression. The OncoTypeDX® gene set consists of 16 genes that have functional relationships to various cancer-related cellular processes and 5 genes that are believed to be constitutively expressed in most cell types and are used to normalize expression across sample sets. OncoTypeDX® calculates a predictive recurrence score using a proprietary algorithm that applies different weights to the individual genes within the gene set. Analyses were performed to compare the OncoTypeDX® 16 gene weighted gene set (OTDX) with a gene set comprised of the same 16 weighted genes plus ASIP (OTDX+ASIP) (Table 2, FIGS. 4-6). These analyses were restricted to the subset of patient samples classified as ESR1+. As expected, the OncoTypeDX® weighted gene set effectively identified groups of patients with early stage ER+ breast cancer that differed significantly in time to progression. Addition of ASIP to the OncoTypeDX® weighted gene set enhanced the prognostic power of that gene set as evidenced by increased separation of the Kaplan Meier survival curves and the associated P values. The observed enhancement by ASIP was most striking in the subset of ER+ breast cancer patients that were treated with TAM following diagnosis and procurement of the tissue samples used in the gene expression analyses (FIG. 6). These data indicate that ASIP can serve as a biomarker of progression that when used in combination with the OncoTypeDX® weighted gene set improves the power of that gene set to identify those patients with early stage breast cancer that are most likely to progress to metastatic disease.

Figure 7:
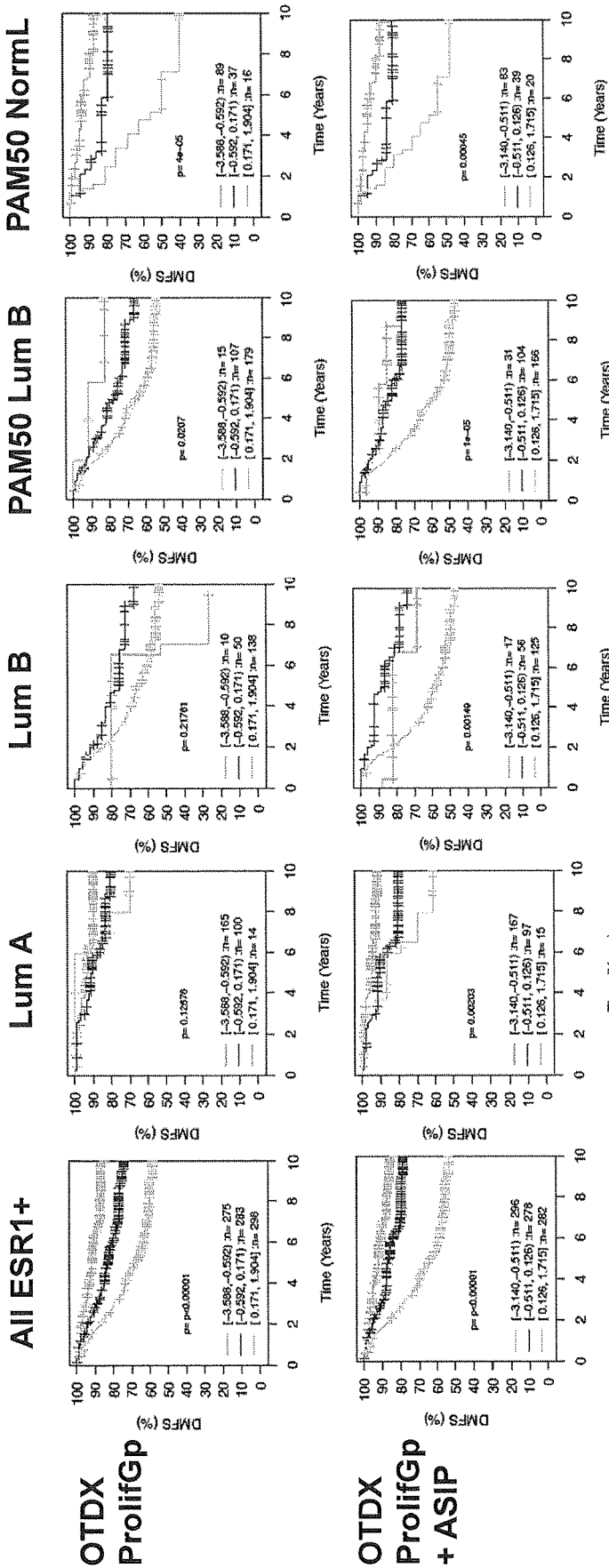
FIG. 7 shows that the addition of ASIP to the OncoType DX® proliferation panel enhances the prognostic power for early stage breast cancer patients.
Figure 8:
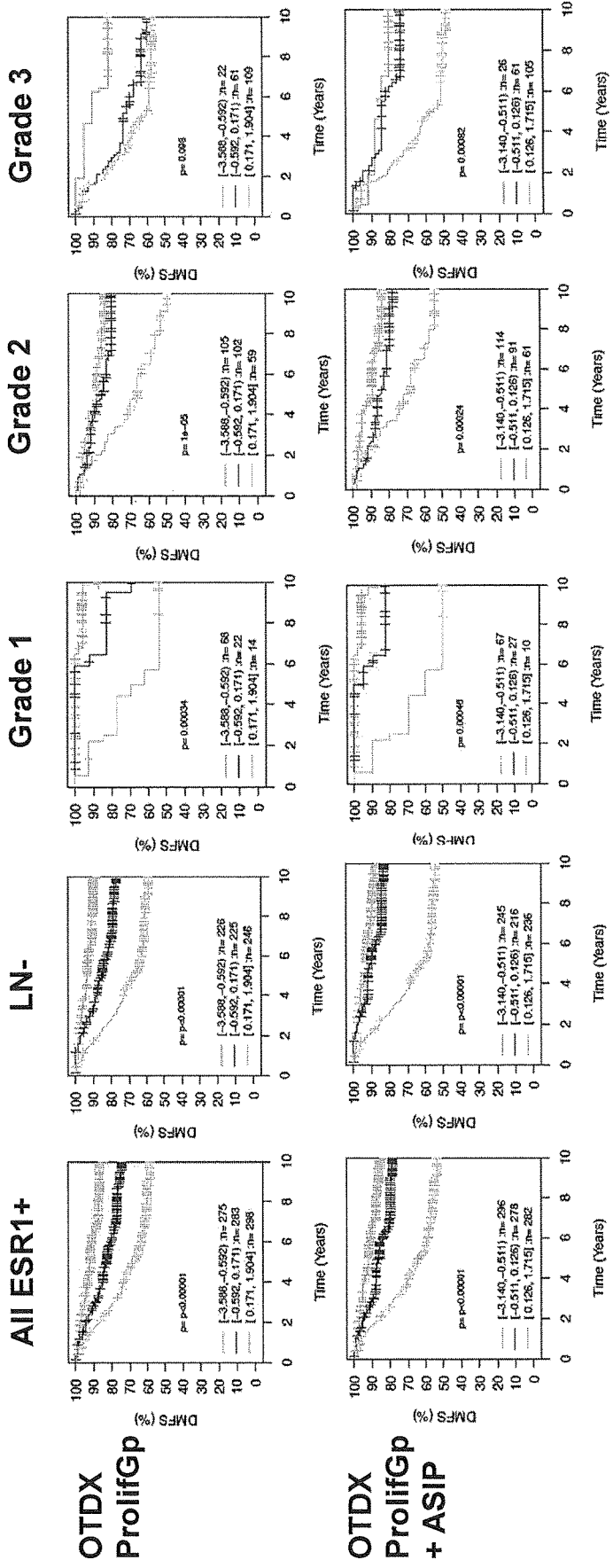
FIG. 8 shows that the addition of ASIP to the OncoType DX® proliferation panel enhances the prognostic power for ESR1+ cancers.
Figure 9:
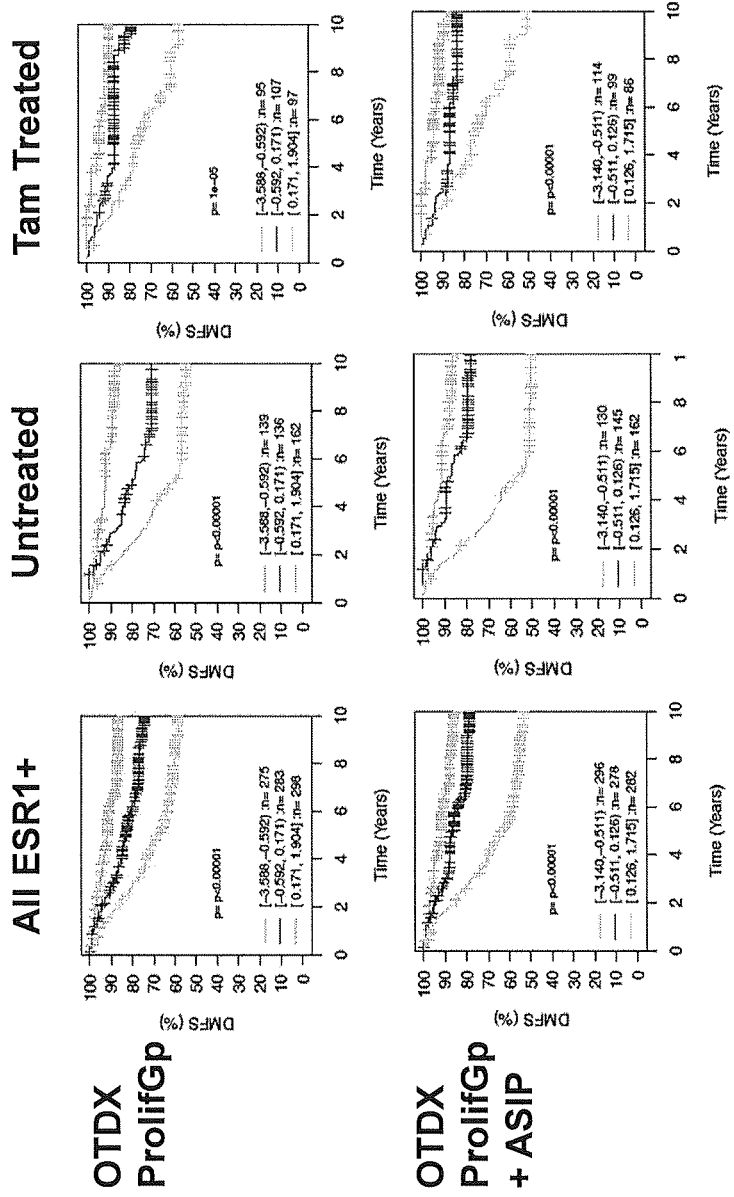
FIG. 9 shows that the addition of ASIP to the OncoType DX® proliferation panel enhances the prognostic power for ESR1+ cancers. Cancers were divided into tamoxifen treated and untreated groups.

Five genes within the OncoTypeDX® weighted gene set comprise the "proliferation group". This 5 gene proliferation group (MKI67, AURKA, BIRC5, CCNB1 or MYBL2) is the most heavily weighted group of genes in the OncoTypeDX® 16 gene weighted gene set and also comprises the backbone of the gene set used by Genomic Health to generate the DCIS recurrence score. Therefore, we evaluated the potential of ASIP to enhance the ability of the OncoTypeDX® proliferation group gene set to predict progression (FIGS. 7-9). Addition of ASIP to the OncoTypeDX® 5 gene proliferation group gene set enhanced the prognostic power of that gene set as evidenced by increased separation of the Kaplan Meier survival curves and the associated P values. The observed enhancement by ASIP addition was striking for all ESR1+ cancers as well as for the subset of ER+ breast cancer defined as LumB, PAM50 LumB (FIG. 7), LN−, Grade 3 (FIG. 8), untreated and Tam treated (FIG. 9). These data indicate that ASIP can serve as a biomarker of progression that when used in combination with the OncoTypeDX® 5 gene proliferation group improves the power of that gene set to identify those patients with early stage breast cancer that are most likely to progress to metastatic disease, and further indicate that ASIP may also be a biomarker for predicting recurrence of ductal carcinoma in situ.

Example 3: ASIP Improves the Predictive Power of PAM50—Prosigna®—Nanostring Technologies The PAM50 gene panel is an established set of 50 genes whose level of expression is used to assign individual breast cancers into defined subtypes that differ in their clinical behavior. A subset of the patient samples accessible through the GOBO informatics tool were annotated with respect to PAM50 subtype. Therefore, we evaluated the ability of ASIP and other MSN genes to identify breast cancer samples within the defined PAM50 subtypes that differ in their clinical behaviors based on time to progression; i.e., DMFS. ASIP expression was significantly inversely associated with DMFS (i.e., high expression—rapid progression) in the subset of patient samples defined as Luminal B using the PAM50 gene panel ($p=0.00077$; $n=358$)(FIG. 1). No significant associations were observed between ASIP expression and DMFS in the PAM50 Basal ($p=0.88$, $n=251$), PAM50 HER2 ($p=0.44$, $n=166$), PAM50 Luminal A ($p=0.13$, $n=323$) or PAM50 Normal-like ($p=0.49$, $n=211$) breast cancer subtypes (data not shown). These data indicate that ASIP has value as a biomarker for predicting progression of breast cancers defined as Luminal B using the PAM50 gene panel. In addition, expression of MC5R ($p=0.027$, $n=135$) and POMC ($p=0.022$, $n=210$) were inversely correlated with DMFS in PAM50 Normal-like breast cancers, indicating their potential as biomarkers in this breast cancer subtype.

Example 4: ASIP Improves the Predictive Power of MammaPrint

Figure 10:
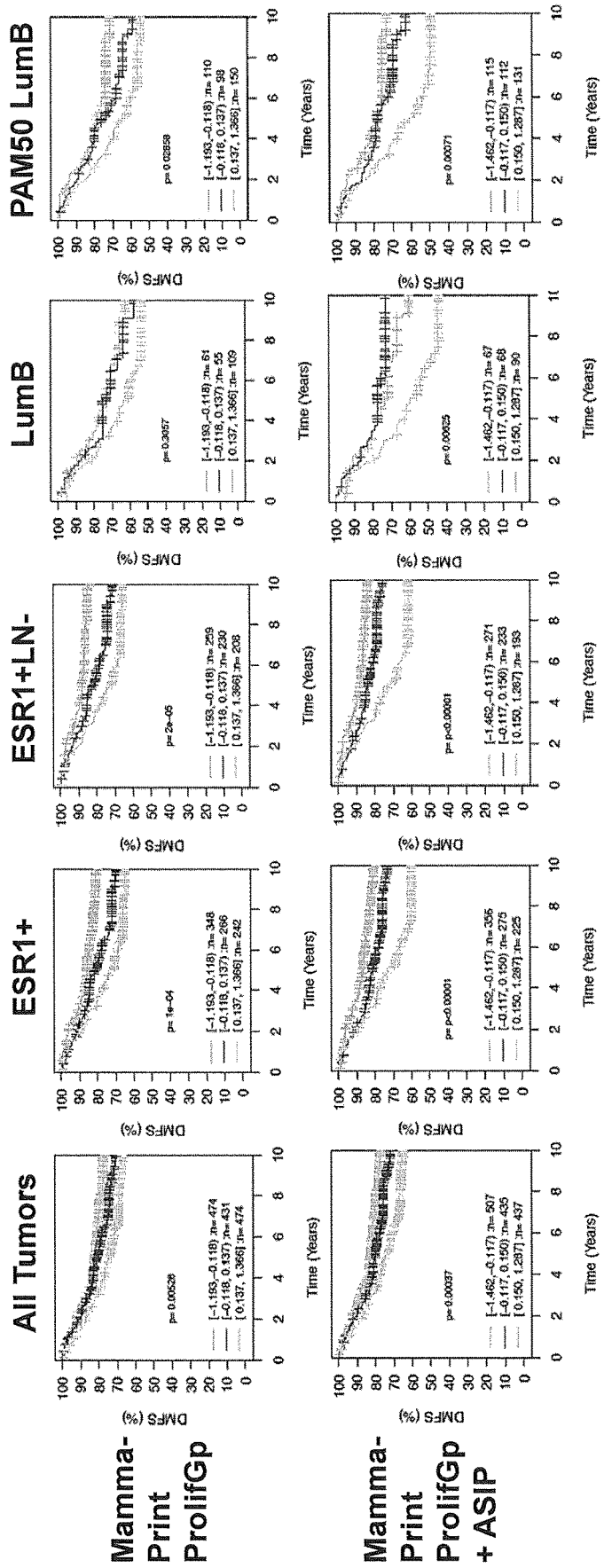
FIG. 10 shows that the addition of ASIP to the MammaPrint proliferation group enhances the prognostic power.

MammaPrint is a 70 gene set microarray based tool that predicts clinical behavior of breast cancer. The genes within the MammaPrint gene set have been annotated relative to the "hallmarks" of cancer. Addition of ASIP to the MammaPrint "proliferation" gene group enhanced the ability of that gene group to predict progression of early stage breast cancers as evidenced by increased separation of the Kaplan Meier survival curves and the associated P values (FIG. 10). Although this enhancement was statistically significant when all breast cancers were evaluated, enhancement was strongest in the ESR1+, ESR1+LN−, LumB and PAM50 LumB subsets of breast cancers.

Example 5: ASIP Improves the Predictive Power of Mammostrat®

Figure 11:
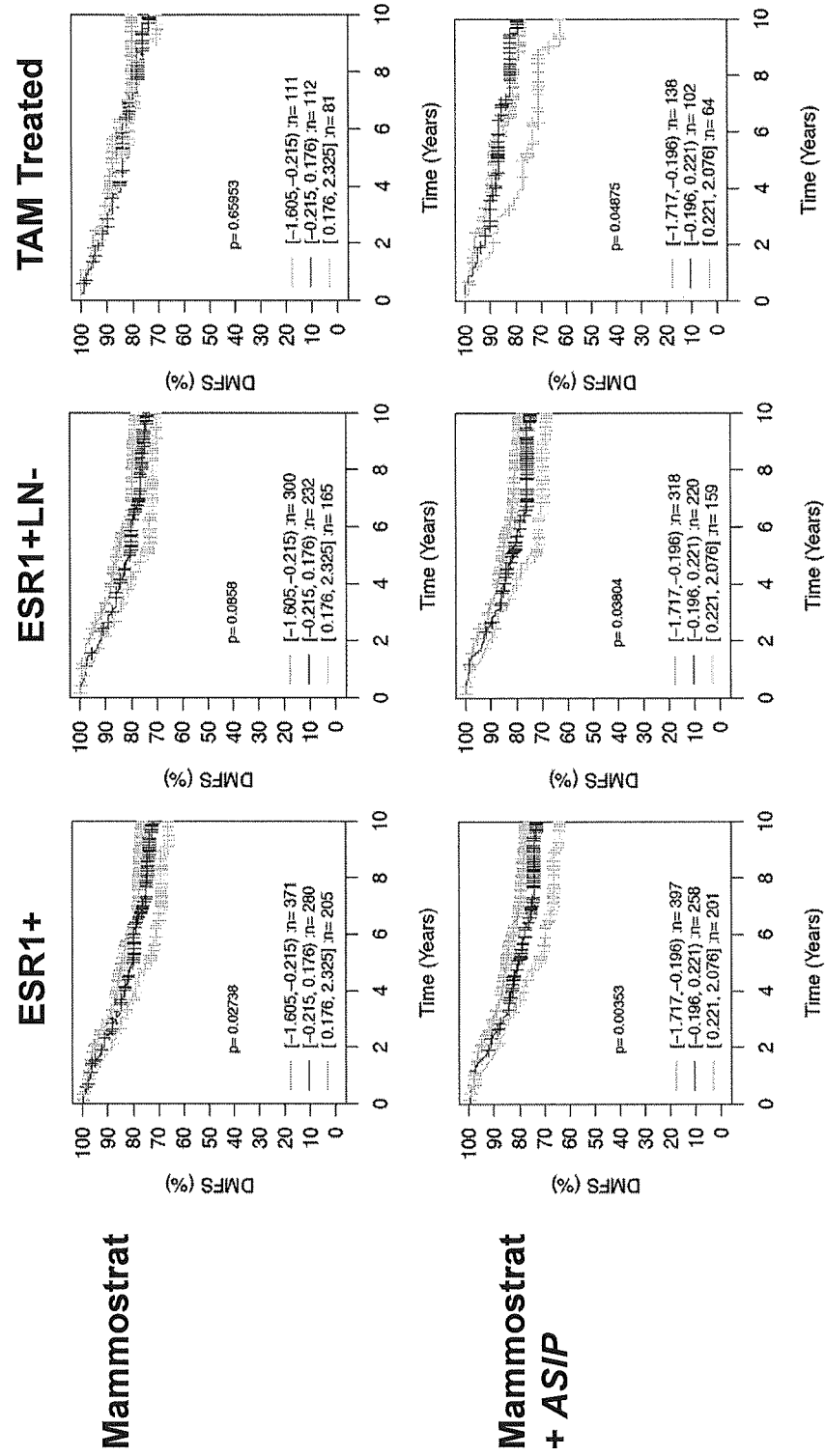
FIG. 11 shows that the addition of ASIP to the Mammostrat assay enhances the prognostic power.

Mammostrat® is a prognostic tool that predicts risk of recurrence of breast cancer based on quantification by immunohistochemistry of expression of five proteins in breast cancer cells. Although Mammostrat® evaluates protein expression in breast cancer cells specifically, the test was developed based on quantitative data on mRNA expression from whole breast cancers. Therefore, we evaluated the ability of the Mammostrat® 5 gene set, without and with ASIP added, to predict breast cancer progression using publically available mRNA expression data and the GOBO informatics tool. Addition of ASIP to the Mammostrat 5 gene set enhanced the ability on this gene set to predict progression of early stage breast cancers as evidenced by increased separation of the Kaplan Meier survival curves and the associated P values (FIG. 11). The enhancement by ASIP was apparent in those cancers classified as ESR1+ and ESR1+LN−, as well as in those patients treated with tamoxifen. These data indicate that ASIP can serve as a biomarker of progression that when used in combination with the Mammoprint® gene set improves the power of that gene set to identify those patients with early stage breast cancer that are most likely to progress to metastatic disease.

The term "polynucleotide," when used in singular or plural, generally refers to any polyribonucleotide or polydeoxribonucleotide, which may be unmodified RNA or DNA or modified RNA or DNA, and single-stranded double-stranded and triple stranded DNA and RNA, as well as RNA and RNA having both single- and double-stranded regions. The term "oligonucleotide" refers to a relatively short polynucleotide.

The terms "differentially expressed gene," "differential gene expression" and their synonyms, which are used interchangeably, refer to a gene whose expression is activated to a higher or lower level in a subject suffering from a disease, specifically cancer, such as breast cancer, relative to its expression in a normal or control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10934590B2). An electronic copy of the "Sequence Listing" will also be available from the USPTO upon request and payment of the fee set forth in 37 CFR 1.19(b)(3).

The invention claimed is:

1. A method of treating a female patient with DCIS or early stage breast cancer, comprising
providing a breast tumor sample from the female patient;
determining the expression level of ASIP, MKI67, AURKA, BIRC5, CCNB1 and MYBL2 in the breast tumor sample to provide test ASIP, MKI67, AURKA, BIRC5, CCNB1 and MYBL2 expression levels;
comparing the test ASIP, MKI67, AURKA, BIRC5, CCNB1 and MYBL2 expression levels to reference ASIP, MKI67, AURKA, BIRC5, CCNB1 and MYBL2 expression levels that are indicative of a progression to metastatic disease;
determining that the test ASIP, MKI67, AURKA, BIRC5, CCNB1 and MYBL2 expression levels are equal to or greater than the reference ASIP, MKI67, AURKA, BIRC5, CCNB1 and MYBL2 expression levels; and
administering aggressive breast cancer treatment.

2. The method of claim 1, wherein the expression level is an mRNA level, a protein level, or the level of a cell biomarker.

3. The method of claim 2, wherein the mRNA level is determined by quantitative PCR or in situ hybridization.

4. The method of claim 1, wherein the comparing the test ASIP expression level to a reference ASIP expression level that is indicative of a likely progression to metastatic disease comprises entering the test ASIP expression level into a predictive algorithm that provides an expression score based on the reference ASIP expression level that is indicative of a likely progression to metastatic disease.

5. The method of claim 4, wherein the predictive algorithm comprises an expression signature of the breast tumor sample.

6. The method of claim 1, wherein the breast tumor sample is determined to be a luminal B tumor, an estrogen receptor positive tumor, or a lymph node negative tumor.

7. The method of claim 1, wherein the female human patient has not been treated with tamoxifen prior to obtaining the breast tumor sample.

8. The method of claim 1, wherein when it is determined that the female human patient is likely to progress to metastatic disease, administering aggressive breast cancer treatment.

9. The method of claim 1, wherein a weighting factor of +1.04 is used for the test ASIP expression level, test MKI67 expression level, test AURKA expression level, test BIRC5 expression level, test CCNB1 expression level and test MYBL2 expression level when determining that the test ASIP, MKI67, AURKA, BIRC5, CCNB1 and MYBL2 expression levels are equal to or greater than the reference ASIP, MKI67, AURKA, BIRC5, CCNB1 and MYBL2 expression levels.

* * * * *